United States Patent [19]

Lazzara et al.

[11] Patent Number: 5,022,860
[45] Date of Patent: * Jun. 11, 1991

[54] ULTRA-SLIM DENTAL IMPLANT FIXTURES

[75] Inventors: Richard J. Lazzara, Lake Worth; Keith D. Beaty, West Palm Beach, both of Fla.

[73] Assignee: Implant Innovations, Inc., West Palm Beach, Fla.

[*] Notice: The portion of the term of this patent subsequent to Mar. 19, 2008 has been disclaimed.

[21] Appl. No.: 283,977

[22] Filed: Dec. 13, 1988

[51] Int. Cl.$^5$ ............................................. A61C 13/00
[52] U.S. Cl. .................................................. 433/174
[58] Field of Search ........................ 433/174, 221, 173

[56] References Cited

U.S. PATENT DOCUMENTS

| 4,406,623 | 9/1983 | Grafelmann et al. | 433/174 |
| 4,626,214 | 12/1986 | Artal | 433/174 |
| 4,668,191 | 5/1987 | Plischka | 433/174 |
| 4,713,003 | 12/1987 | Symington et al. | 433/173 |
| 4,863,383 | 9/1989 | Grafelmann | 433/174 |

FOREIGN PATENT DOCUMENTS 2199502 7/1988 United Kingdom ................ 433/174

Primary Examiner—Cary E. Stone
Attorney, Agent, or Firm—Alfred H. Rosen

[57] ABSTRACT

Dental implant fixtures having external diameters less than 3.0 mm., and external threads which are deeper at the apical end of the fixture than elsewhere are described. The deeper threads near the apical end serve to pull the fixture into a prepared bore in the patient's jawbone. There results a firm close contact between the fixture and the host bone to promote osseointegration. Ultra-slim implant fixtures are provided which can be used in thin sections of human jawbone where dental implants were previously contra-indicated.

8 Claims, 1 Drawing Sheet

ULTRA-SLIM DENTAL IMPLANT FIXTURES

BACKGROUND OF THE INVENTION

This invention relates to dental implant fixtures, more particularly to cylindrical fixtures which have a smaller external diameter than has up to now been available, for use in thin sections of human jawbones.

Cylindrical-shaped dental implant fixtures are known; they are in two broadly-defined groups —some having screw threads on all or part of the exterior wall, and some without threads. All are fitted into a pre-drilled bore prepared in the patient's jawbone, those with screw threads being screwed in, like a machine screw. Of the latter, some are self-tapping, and in some cases the prepared bore is pre-tapped to receive the threaded implant. In all cases the thickness of the section of the patient's jawbone to be prepared limits the diameter of the prepared bore that can be drilled in it. It is general dental practice to leave at least one mm. thickness of jawbone wall on either side of the prepared bore. Up to now cylindrical dental implant fixtures have been available in diameters ranging from about 4.0 mm. down to about 3.3 mm. This has limited the thickness of human jawbones in which dental implant fixtures can be installed to not less than about 5.3 mm., effectively barring the availability of dental implant fixtures in many situations where periodontic restoration is otherwise indicated.

Placement of implants in narrow ridges often is only possible if bone is removed; i.e.: cutting away of the narrow ridge until a point of sufficient ridge-width to accept the implant is reached. Availability of a narrow implant will reduce, and in some cases eliminate the need for such a procedure.

Dental implant fixtures are fitted with bores to receive and support transition components which in turn support a prosthodontic restoration. In the case of a cylindrical-shaped fixture this bore is usually coaxial in the fixture; frequently it is internally-threaded. The thickness of the material of the fixture between the outer wall (minor diameter of the external thread) and the wall of the receiving bore at its major diameter cannot be reduced below the minimum strength requirements of the fixture and its related transition components. Up to now these requirements have contributed to the above-mentioned smaller diameter of about 3.3 mm.

GENERAL DESCRIPTION OF THE INVENTION

The princial object of this invention is to provide a generally cylindrical dental implant fixture which has a smaller exterior diameter than has been available previously, so that dental implant fixtures will be able to be installed in thinner sections of human jawbones than has previously been possible. To accomplish this object the invention provides a new, thinner dental implant fixture having a new configuration of implant body and external screw threads, as well as a new combination of the implant fixture and a prepared bore specially contoured to receive it. The implant body is in the form of a tapered (e.g.: cone-shaped) male shaft having screw threads on its exterior. The threads are of uniform pitch. The peaks of the threads lie on the locus of a cylinder that is coaxial with the tapered shaft, while the roots of the threads are truncated on the surface of the tapered shaft. The shaft extends between a gingival region of the implant fixture and an apical end, the wider end of the shaft being in the gingival region. The diameter of the wider end of the shaft is preferably not larger than the diameter of the cylinder locus of the thread peaks. Thus, the narrower end of the shaft is at the apical end of the implant fixture, where the threads have maximum peak-to-trough depth. As the threads progress axially away from the tail end, peak-to-trough depth diminishes, the shaft becomes wider, and surface space on the shaft between adjacent threads increases. The result of the taper, or diminishing peak-to-trough dimensions is a thicker wall or area of material between the internal bore thread (major diameter) and the external thread (minor diameter). This thicker wall is in the areas of highest stress on the implant fixture; it allows the fabrication of a 2.8 to 2.9 mm. implant which meets minimum strength requirements. With this combination of cylindrical-peak threads on a male tapered shaft the threads can engage the bottom side walls of a bore to pull the shaft tightly into the bore, at the same time bringing the shaft into intimate contact with the entire side walls of the prepared bore. Preferably the prepared bore is tapered to mate with the taper of the shaft when the latter is fully seated in the bore.

Dental fixtures according to the invention provide, in combination, two recognized means for promoting osseointegration of a dental implant fixture in human jawbone. The threads with increasing purchase at the apical end of the fixture serve to anchor the fixture at the side walls of the prepared bore well inside the jawbone near the bottom of the bore. This anchor effect immobilizes the implant fixture during the healing period, satisfying a well-recognized requirement for successful osseointegration. The side walls of the shaft are brought into intimate proximity with the side walls of the prepared bore where the two can be held relatively fixed together for a sufficient time to allow osseointegration to take place. The wider part of the shaft being near the gingival aspect of the jawbone maintains this intimate contact during and after the osseointegration process. Failure to maintain good contact between the implant fixture and the bone tissue near the gingival aspect of the jawbone has in the past led to bone resorption in that region with the use of some prior-art dental implant fixtures. This invention is, accordingly, useful not only to satisfy its principal object but also to improve dental implant fixtures in general.

Dental implant fixtures according to the invention can be made significantly less than 3.00 mm. in shaft diameter. In one example a tapered shaft has an apical-end diameter of 2.21 mm., and a gingival-region diameter of 2.90 mm. The screw threads on the shaft have a peak diameter of 2.90 mm.

Figure 3:
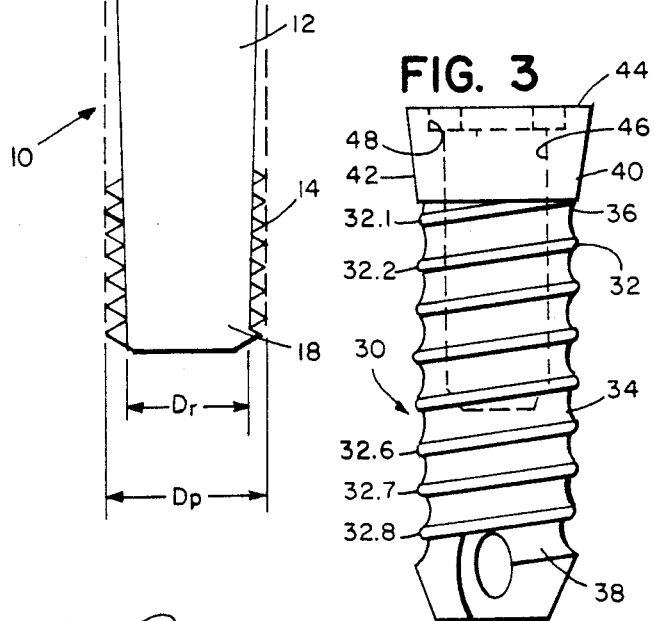
FIG. 3 is a longitudinal side view of another dental implant fixture according to the invention.
Figure 4:
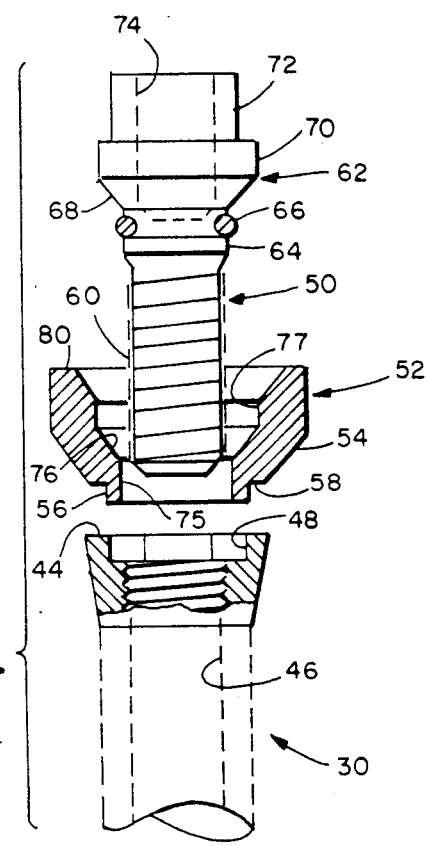
Figure 5:
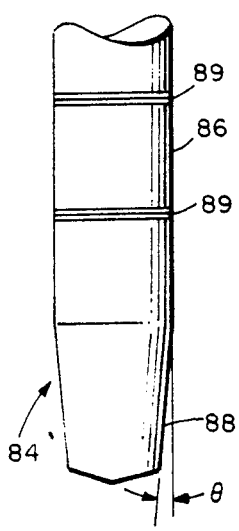
Figure 6:
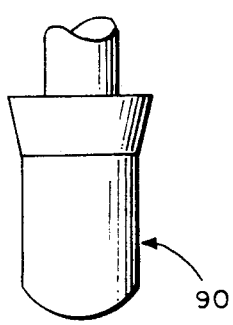
Figure 3A:
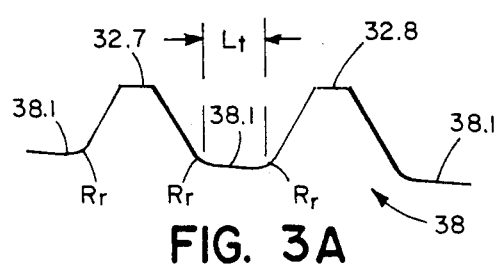

FIG. 3A schematically illustrates a detail of the screw-thread configuration of the fixture of FIG. 3;

FIG. 4 is an expanded side view of a coronal fitting for use with the fixture of FIG. 3;

FIG. 5 is an outline view of a bone drill for preparing a female bore to accept an implant fixture of the invention; and FIG. 6 is an outline view of a counter-sink useful to prepare a bore to accept such a fixture.

Figure 1:
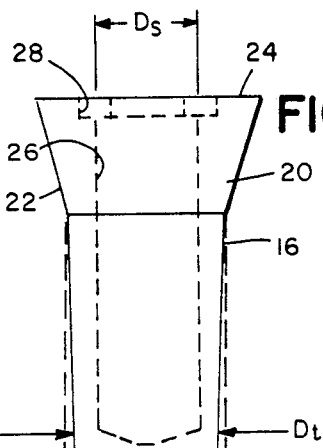
FIG. 1 is a longitudinal side view of a dental implant fixture according to the invention.
Figure 2:
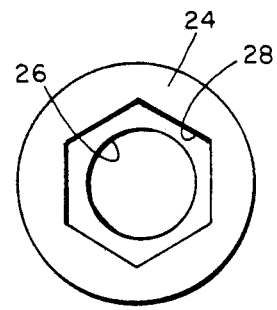
FIG. 2 is an end view of the gingival aspect of the implant fixture illustrated in FIG. 1.

Referring now to FIGS. 1 and 2, the dental implant fixture 10 has a conically-tapered main body shaft 12 bearing screw-threads 14 having peaks on a cylindrical locus of diameter Dp. The roots of the screw threads are truncated on the locus of the cone which defines the taper of the shaft 12. At the gingival region 16 of the shaft the cone has a diameter that is the same as or slightly more than the diameter Dp of the thread-peak cylinder. At the apical end 18 of the shaft the cone is tapered down to a smaller diameter Dr. The threads 14 are accordingly deeper at the apical end 18 than at the gingival end 16 of the shaft. A smooth-sided cap 20 at the gingival end of the shaft completes the fixture. The sides 22 of this cap are smooth and taper outwardly toward the gingival surface 24 of the fixture 10. A receiving bore 26 proceeding axially into the fixture from the gingival surface is provided for receiving a fitting for supporting a prosthodontic restoration (not shown). A non-circular, here hexagonal-shaped, female socket 28 in the gingival surface 24 surrounds the opening into the receiving bore, for providing anti-rotation to such a fitting (e.g.: as is illustrated in FIG. 4). The choice of a female socket 28 contributes to successfully making a small-diameter implant fixture. The diameter of the shaft 12 at the bottom of the bore 26 is marked Dt.

The tapered shape can be applied to the shaft 12 continuously from its gingival end to its apical end. Alternatively, the shaft can be partly cylindrical and partly tapered, as in the embodiment illustrated in FIG. 3. The implant fixture 30 of FIG. 3 has a single-lead thread 32 coiled around the shaft 34 with substantial shaft surface exposed between successive turns 32.1 -32.8 of the thread. The spacing between successive turns of the thread 32 may be approximately the same as, or greater than, the thread-root thickness. The shaft is cylindrical from its gingival end 36, from turn 32.1 to turn 32.6, following which the shaft tapers toward its apical end 38. Two turns 32.7 and 32.8 are borne on the tapered portion of the shaft. In general, the fixture 30 is conical at the apical end 38, but blends into a cylindrical section, just apical of the internal bore 46. The purpose of this contour is to preserve a minimum wall thickness fo the fixture around the bore 46, while maintaining full thread depth at the apical end. This is also a convenient form to manufacture.

FIGS. 3A is an expanded view showing the contours of the final two turns 32.7 and 32.8 and the tapering shaft surface portion 38.1 beside and between them. On the tapering surface 38.1 the threads are deeper than the threads on the cylindrical portion of the shaft, toward its gingival end 36. The roots of the threads curve gradually into the sidewall of the shaft 38.1 on a radius Rr; this feature is used along the entire length of the shaft. There are no sharp-angled meeting surfaces, so that stress concentrations are reduced, which minimizes the chances of breaking the ultra-slim implant fixture.

As in FIG. 1, the implant fixture 30 of FIG. 3 has a gingival cap 40 with tapering smooth sides 42, a gingival surface 44, an axial receiving bore 46 opening into the fixture through the gingival surface and a non-rotational female socket 48 in the gingival surface around the opening into the bore. The receiving bore 46 is internally threaded, to receive an abutment screw 50 specially dimensioned for this fixture which is shown in FIG. 4.

To permit the use of existing parts and components that are in use for mounting prosthodontic restorations to dental implant fixtures, the invention provides a transition component 52 from the ultra-small size of the new fixture 30 to the normal size of such components. As illustrated in FIG. 4, the invention shows a transition that is useful in the well-known and widely-used implant systems. The transition component 52 replaces a prior transmucosal component dimensioned to cooperate with the prior larger-diameter implant fixtures. This new component 52 has a small diameter at its lower end 54 to mate with the gingival surface 44 of the implant fixture. A hexagonal boss 56 fits snugly into the female socket 48; this boss is slightly shorter than the depth of the socket so that a shoulder 58 around the boss can meet the gingival surface 44 when the transition component 52 is fitted to the fixture 30. Use of the female socket 48 in the gingival surface 44 provides a larger area of gingival surface to meet the shoulder than would be provided if a male non-rotational fitting were used on the fixture 30.

The abutment screw 50 has a threaded bolt 60 which screws into the receiving bore 46. The head 62 of the abutment screw has, proceeding supragingivally, in order, a grooved shaft 64 bearing an O-ring 66, an expanding-taper section 68, a cylinder section 70 and a nut section 72 useful for turning the abutment screw 50 into the bore 46. A second bore 74 in the head is dimensioned to receive a standard "gold screw" of the kind used in the prior systems (not shown). Internally, the transition component 52 has a tapered surface 76 which tapers on the same angle as the expanding taper 68, a smaller cylindrical bore 75 at the narrower end of the tapered surface 76 and a larger cylindrical bore 77 at the wider end of the tapered surface 76. When the abutment screw is turned fully into the receiving bore 46 the expanding taper 68 of the head 62 seats on the tapered surface 76 and the grooved shaft 64 fits into the smaller bore 75, where the O-ring provides a seal. The cylinder section 70 of the head 62 comes to rest in the larger bore 77 and the nut section 72 extends out of the transition component 52 beyond the supragingival surface 80 of the latter component. This supragingival surface is dimensioned to accept a standard gold cylinder (not shown) as used in the existing implant systems to support a prosthodontic restoration.

While use of the invention has been illustrated in connection with currently-available implant systems, it will be understood that the invention can be practiced with any other system now or future existing.

To achieve the objects of the invention careful attention was given to dimensions and materials chosen. Dimensionally, the design is based on the need to:

1—use as large an abutment screw as possible —the bolt 60 has a diameter of 1.8 mm. at the thread peaks; and
2—keep the implant thread-peak diameter to 2.9 mm. or smaller. Typical dimensions of the fixture shown in FIG. 1 are: Ds 1.8 mm.; Dp 2.80 mm.; Dr 2.21 mm.; and Dt 2.56 mm. In FIG. 3A, Lt 0.36 mm., and Rr 0.05 mm. However, as is mentioned above, Lt may be larger than the thread-root thickness. Owing to the ultra-small diameter of the new fixture, pure titanium was deemed inadequately strong; a stronger alloy is preferred. A suitable alloy is "TiA16-4V".

Taking into consideration the convenience of oral surgeons and periodontists, to whom the invention is addressed, the new implant fixture is preferably self-tapping, and its shape does not require a special surgical drill for each implant length. Implant fixtures according to the invention can be provided in a variety of lengths, e.g.: 8, 10, 13 and 15 mm. A bone drill 84 contoured as shown in FIG. 5 can be used for all such lengths. The main drill shaft 86 is of uniform diameter and the apical end 88 is tapered, conforming in this illustration to the shape of the implant fixture 30 shown in FIG. 3. Depth bands 89 are marked on the main shaft 86, one for each depth of prepared bore intended to be drilled. A counter-sink 90 shown in outline in FIG. 6 can provide a tapered opening into the prepare bore in the jawbone (not shown) conforming (for example) to the shape of the gingival cap 40, so that the side walls of the implant fixture will everywhere be in contact with the host bone.

When a suitable prepared bore is drilled in the host jawbone, the shaft of the implant fixture will fit snugly into it, and the threads of the fixture will tap into the adjacent bone. Near the apical end of the shaft the threads are deeper and will cut more deeply into the side walls of the prepared bore; near the bottom of the prepared bore the diameter is smaller, owing to the tapered apical end 88 of the drill. This combination of deeper threads at the apical end of the fixture and more bone for them to cut into near the bottom of the prepared bore provides increased thread engagement between the fixture and the bone deep within the bore, and a strong anchor to hold the fixture immobile during the healing process. Elsewhere the threads help to anchor the fixture against axial movement in the prepared bore, while intimate contact between the fixture and the host bone provides the best-known environment for osseointegration to proceed. To this end, the side-walls of the gingival cap 20, 40 are highly polished; in addition, the matching taper provides between the cap and the prepared bore, by use of the countersink 90, pulled together by the threads, provides enhanced environment for successful osseointegration.

We claim:

1. A dental implant fixture having an implant shaft for implantation in a specially prepared bore in a patient's jawbone, said prepared bore extending from a gingival apsect of said jawbone to an interior region within said jawbone, said shaft extending between a gingival region and an apical end which reaches to said interior region when said shaft is installed in said prepared bore with said gingival region located at said gingival aspect, said shaft having on its exterior screw thread means the root-to-peak depth of which is greater at said apical end than at said gingival end, the peaks of said screw threads being on the locus of a cylinder extending from said apical end toward said gingival region, said shaft being tapered over at least part of its axial length to a reduced diameter at its apical end, so as to provide a tapered make shaft at the roots of said threads having said exterior threads with peaks on a cylindrical locus, the wider end of said shaft being toward said gingival end, said fixture having a receiving bore opening through said gingival region and extending along the tubular axis of said fixture from said gingival region toward said apical end to terminate in a location between said gingival region and said apical end, for receiving prosthodontic support means, wherein the diameter of said cylindrical locus is less than 3.00 mm., the diameter of said shaft at the roots of said screw threads is in the range from about 2.2 mm. at said apical end to not substantially greater than said cylindrical locus toward said gingival end, the root diameter of said shaft at said location is about 2.5 mm., and the internal major diameter of said receiving bore is about 1.8 mm.

2. A dental implant fixture according to claim 1 in combination with a specially prepared bore that is tapered to a smaller diameter in said interior region and configured to mate with said tapered male shaft when said shaft is screwed into said prepared bore with said thread means having the greater thread-to-peak depth engaging substantially to their full depth in the bone tissue surrounding said bore.

3. A dental implant fixture according to claim 1 in which said screw thread means consists essentially of a single thread coiled around said shaft with adjacent turns spaced axially apart on said shaft a distance which is at least approximately as great as the root thickness of said threads.

4. A dental implant fixture according to claim 3 which said distance is about 0.36 mm.

5. A dental implant fixture according to claim 3 in which said thread is curved at its root gradually into the adjacent surfaces of said shaft, said implant fixture being substantially devoid of sharp-angled meeting surfaces between said thread and the surface of said shaft, so as to avoid stress concentrations in use.

6. A dental implant fixture according to claim 1 in which said shaft is substantially cylindrical from said gingival region to said location, and beyond said location said shaft is tapered to said reduced diameter toward said apical end under the remaining turns of said thread.

7. A dental implant fixture according to claim 1 in which said gingival region includes a head cap which has a smooth side surface devoid of said thread means.

8. A dental implant fixture according to claim 7 in which said cap expands in diameter from said shaft to a gingival-aspect surface which normally lies substantially flush with said gingival aspect of said jawbone when said fixture is installed in said bore.

* * * * *